(12) United States Patent
Brown et al.

(10) Patent No.: US 6,274,567 B1
(45) Date of Patent: Aug. 14, 2001

(54) SELECTION AND/OR ENHANCEMENT OF RESIDENT MICROORGANISMS IN THE GASTROINTESTINAL TRACT

(75) Inventors: Ian L. Brown, Tamworth; Patricia Lynne Conway, La Perouse; Karl Anders Olof Henriksson, Bellevue Hill; Kenneth J. McNaught, Cottage Point; Xin Wang, Randwick, all of (AU)

(73) Assignees: The University of New South Wales, New South Wales; Burns Philp & Company Limited; Burns Philp Research & Development Pty Ltd., both of Sydney; Commonwealth Scientific and Industrial Research Organisation, Campbell; Arnott's Biscuits Limited, Homebush; Gist-Brocades Austrialia Pty Limited, Moorebank; Goodman Fielder Ingredients Limited, Gladesville, all of (AU)

( * ) Notice: Subject to any disclaimer, the term of this patent is extended or adjusted under 35 U.S.C. 154(b) by 0 days.

(21) Appl. No.: 09/155,115

(22) PCT Filed: Mar. 20, 1997

(86) PCT No.: PCT/AU97/00175

§ 371 Date: May 10, 1999

§ 102(e) Date: May 10, 1999

(87) PCT Pub. No.: WO97/34592

PCT Pub. Date: Sep. 25, 1997

(30) Foreign Application Priority Data

Mar. 20, 1996 (AU) ................................ PN8809

(51) Int. Cl.[7] .................. C12N 1/20; A61K 31/715; A23L 1/0522

(52) U.S. Cl. .................. 514/60; 514/54; 514/778; 435/252.1; 462/661; 462/658

(58) Field of Search ............... 435/252.1; 514/60, 514/54, 778; 426/661, 658

(56) References Cited

U.S. PATENT DOCUMENTS

| | | | |
|---|---|---|---|
| 3,657,010 | * | 4/1972 | Michell et al. . |
| 3,998,753 | * | 12/1976 | Antoshkiw et al. . |
| 4,414,238 | * | 11/1983 | Schmidl . |
| 4,885,180 | * | 12/1989 | Cochran et al. . |
| 5,147,668 | | 9/1992 | Munk . |
| 5,455,342 | * | 10/1995 | Redding, Jr. . |

FOREIGN PATENT DOCUMENTS

| | | | |
|---|---|---|---|
| 21247/67 | | 11/1968 | (AU) . |
| 0659769 | | 6/1995 | (EP) . |
| 46024063 | * | 7/1971 | (JP) . |
| WO 94/03049 | * | 2/1994 | (WO) . |
| WO 97/14342 | * | 7/1994 | (WO) . |
| 96/08261 | | 3/1996 | (WO) . |

OTHER PUBLICATIONS

Nutrition Reports International, vol. 15, No. 2, Feb. 1977. Bruns et al, "Effect of Modified Starch on the Microflora of the Small Intestine and Caecum of Rats" pp. 131–138.

* cited by examiner

Primary Examiner—Francisco Prats
Assistant Examiner—Susan D. Coe
(74) Attorney, Agent, or Firm—McDermott, Will & Emery

(57) ABSTRACT

Improved method of enhancing a population of one or more target microorganisms in the gastrointestinal tract of an animal, the improvement comprising providing to the animal a selected modified or unmodified resistant starch or mixtures thereof, such that the one or more microorganisms will selectively utilise the starch and/or increase in number and/or activity in the gastrointestinal tract, either uniformly throughout the gastrointestinal tract or at specific site or regions.

1 Claim, 5 Drawing Sheets

SELECTION AND/OR ENHANCEMENT OF RESIDENT MICROORGANISMS IN THE GASTROINTESTINAL TRACT

TECHNICAL FIELD

This invention relates to an improved method of enhancing a population of one or more target microorganisms in the gastrointestinal tract, especially the small intestine and the large bowel, of animals and humans.

BACKGROUND ART

It is the contention of many scientists that the health and well being of people can be positively or negatively influenced by the microorganisms which inhabit the gastrointestinal tract, and in particular, the large bowel. These microorganisms through the production of toxins, metabolic by-products, short chain fatty acids, and the like affect the physiological condition of the host. The constitution and quantity of the gut microflora can be influenced by conditions or stress induced by disease, life style, travel, and other factors. If microorganisms which positively affect the health and well being of the individual can be encouraged to populate the large bowel, this should improve the physiological well being of the host The present inventors have realised that it would be desirable to provide a medium that would function to promote the growth and/or activity of target microorganisms in the gastrointestinal tract of animals including humans.

DISCLOSURE OF INVENTION

The present invention consists in an improved method of enhancing a population of one or more target microorganisms in the gastrointestinal tract of an animal. the improvement comprising providing to the animal a selected modified or unmodified resistant starch or mixtures thereof, such that the one or more microorganisms will selectively utilise the starch and/or increase in number and/or activity in the gastrointestinal tract.

The target population of microorganism may be enhanced throughout the gastrointestinal tract of the animal or targeted at specific sites of the gastrointestinal tract. It will be appreciated that the present invention will be suitable for any animal that requires alteration of its gastrointestinal flora. The present method is particularly suitable for use in humans.

The starches suitable include resistant or high amylose starches and modified forms thereof. The animal or human may be fed the selected resistant starch or the starch may be incorporated in a probiotic composition.

As used in this specification, "resistant starch" includes those forms defined as RS1, RS2, RS3 and RS4 as defined in Brown, McNaught and Moloney (1995) Food Australia 47: 272–275. Either modified or unmodified resistant starches or mixtures thereof are used in this invention. The advantage of resistant starch is that it is largely not degraded until it reaches the large bowel. Therefore it provides a readily available substrate for fermentation by the target microorganisms as soon as they arrive in the large bowel. In both cases, a preferred form of resistant starch is a high amylose starch particularly high amylose starches as disclosed and taught in WO 94/03049 and WO 94/14342, the contents of which are incorporated into this specification for the purposes of convenient cross-reference.

In WO 94103049 and WO 94/14342, high amylose starches are disclosed which are resistant starches and include maize starch having an amylose content of 50% w/w or more, particularly 80% w/w or more, rice or wheat starch having an amylose content of 27% w/w or more and; particular granular size ranges of starches having an amylose content of 50% or more and enhanced resistant starch content, these starches including maize, barley, and legumes. This invention is not, however, limited to these forms of resistant starch. For example, other forms of resistant starch are derived from sources such as bananas and tubers such as potatoes and modified forms thereof.

It may be advantageous to also chemically modify the starch to, for instance, alter the charge density or hydrophobicity of the granule and/or granule surface to enhance the attachment compatibility between the microorganism and the resistant starch. Chemical modifications, such as etherification, esterification, acidification and the like are well known in this art as being suitable chemical treatments.

To modify the degree of enzyme susceptibility of the resistant starch the conformation or structure of the starch can be altered. Examples include acid or enzyme thinning and cross bonding using difunctional reagents.

The starches may be modified physically by, for example, crystallisation.

It is also within the scope of this invention to subject enzymatically treated resistant starches to chemical modification as described above.

As used herein, Hi-maize™ (trade mark) refers to a high amylose starch obtained from Starch Australasia Limited.

In order that the present invention may be more clearly understood, preferred forms thereof will be described with reference to the following figure and examples.

MODES FOR CARRYING OUT THE INVENTION

EXAMPLE 1

Figure 1:
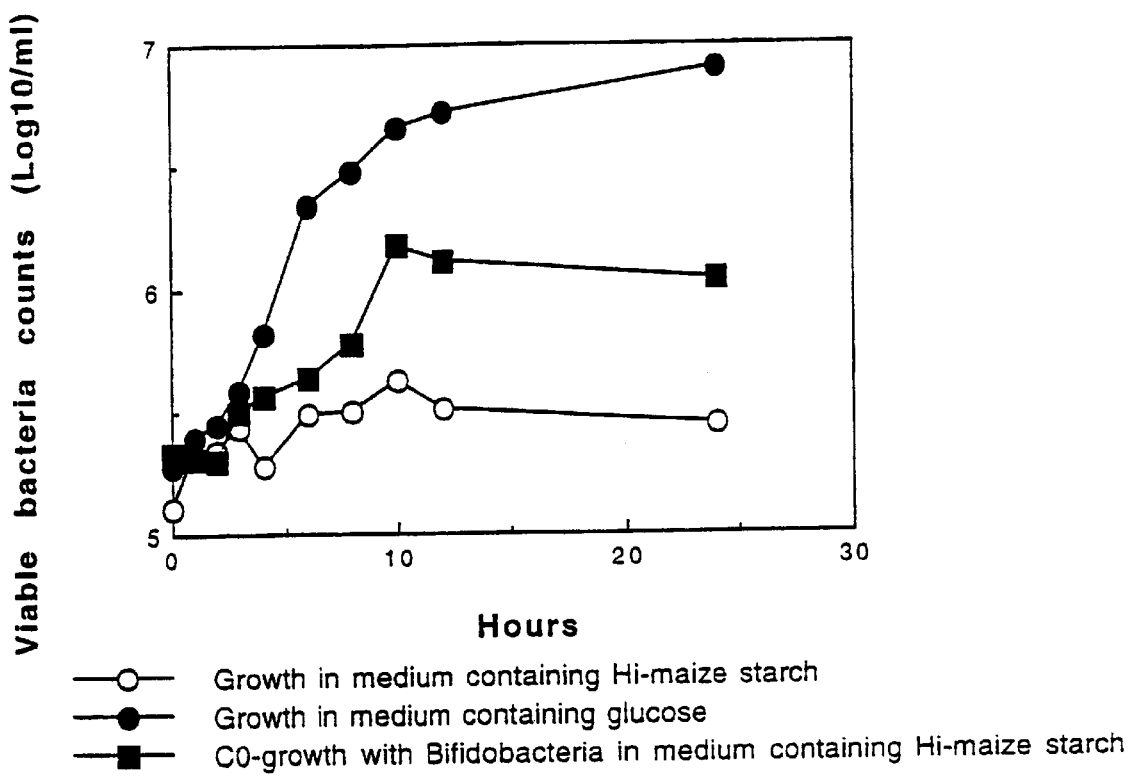
FIG. 1 shows comparison of the co-culturing of *Lactobacillus acidophilus* with *Bifidobacterium* strain X8AT2 in glucose and amylose starch medium.

By measuring the amylase activity of specific intestinal bacteria when grown in standard laboratory medium containing glucose, starch (amylopectin) or resistant starch (amylose) added to a defined medium (composition included in Table 1 at a final concentration of 10 mg/ml), one can show that many of the intestinal bacteria produce amylase which can utilise the resistant starch (Table 2). In addition, the specific growth rates when six different intestinal bacteria were grown on glucose, amylose, amylopectin, Hi-maize™ and carboxymethylated resistant starch were determined (Table 3). The various bacteria tested grew at very different rates to each other, indicative that individual bacterial groups or species will be selectively enhanced by the form of starch used.

TABLE 1

Composition of medium used for growing intestinal strains of bacteria.

| Ingredient | Amount |
|---|---|
| Bacteriological peptone | 7.5 g |
| Yeast extract | 2.5 g |
| Tryptone | 5.0 g |
| Starch | 10.0 g |
| $K_2HPO_4$ | 2.0 g |
| $KH_2PO_4$ | 1.0 g |
| $NaHCO_3$ | 0.2 g |
| $NaCl_2$ | 2.0 g |
| $MgCl_2$ | 0.2 |
| $CaCl_2$ | 0.2 g |
| $MnCl_2$ | 0.02 g |
| $CoCl_2$ | 0.02 g |
| Cystein | 0.5 g |
| $FeSO_4$ | 0.005 g |
| Tween 80 | 2 ml |
| Hemin | 0.005 g |
| Vit $B_{12}$ | 0.001 g |
| Vit K | 0.0005 g |
| Water (final volume) | 1 liter |

TABLE 2

Amylase activity after growth of intestinal isolates on starch and resistant starch.

| Bacteria | Glucose | Amylopectin | Amylose |
|---|---|---|---|
| 1. Supernatant | | | |
| Cl. butyricum | 0.592 | 0.987 | 0.317 |
| Bact. fragilis | 0.064 | 0.563 | 0.927 |
| Bif. bifidum | 0.506 | 0.131 | 0.293 |
| Bif. pseudolongum | 0.087 | 0.542 | 0.423 |
| E. limosum | 0.202 | 0.568 | 0.794 |
| Bact. vulgatus | 0.196 | 0.602 | 0.380 |
| 2. Cell Extract | | | |
| Cl. butyricum | 0.000 | 0.000 | 0.021 |
| Bact. fragilis | 0.045 | 1.038 | 2.018 |
| Bif. bifidum | 0.295 | 4.271 | 9.270 |
| Bif. pseudolongum | 0.664 | 3.855 | 12.685 |
| E. limosum | 0.375 | 0.491 | 0.039 |
| Bact. vulgatus | 0.229 | 1.644 | 3.381 |

TABLE 3

Specific growth rates.

| Bacteria | Glucose | Amylose | Amylopectin | Hi Maize | Modified starch A 955 D2 |
|---|---|---|---|---|---|
| Cl. butyricum | 1.348 | 1.091 | 1.326 | 1.071 | 0.986 |
| Bif. bifidum | 0.8.6 | 0.509 | 0.721 | 0.746 | 0.704 |
| Bif. pseudolongum | 0.807 | 0.575 | 0.712 | 0.692 | 0.658 |
| Bact. vulgatus | 0.834 | 0.331 | 0.680 | 0.501 | 0.598 |
| Bact. fragilis | 0.645 | 0.355 | 0.490 | 0.398 | 0.448 |
| E. limosum | 0.570 | 0.338 | 0.632 | 0.421 | 0.320 |

EXAMPLE 2

A number of modifications of the resistant starch (Hi-maize™) (Table 4) were used in the defined growth medium presented in Table 1. The intestinal isolates were then inoculated and the starch concentration determined ned after 22 h incubation as an indication of the extent of utilisation. Total carbohydrate was estimated using phenol-sulphuric acid assay. Surprisingly, a modification often resulted in altered utilisation of the starch as can be seen in Table 5.

TABLE 4

Starch identification

| Starch | Destination | Identification | Analysis |
|---|---|---|---|
| 1 | A939 (D19) | Hydroxypropylated | DS* = 0.13 |
| 2 | A938 (C79) | Acetylated | Acetyl value = 2.69% |
| 3 | A961 (D8) | Octenyl succinated | OSA value = 4.73% |
| 4 | A955 (D2) | Carboxymethylated | Carboxyl value = 1.0% |
| 5 | A960 (D7) | Succinated | Succinyl value = 3.97% |
| 6 | HA 008 (D2118) | Unmodified | — |
| 7 | A993 D42 | Succinated | Succinyl value = 4.1% |
| 8 | A956 (D1) | Carboxymethylated | Carboxyl value = 2.0% |
| 9 | A995 (D57) | Acetylated | Acetyl value = 4.0% |
| 10 | A965 (D9) | Hydroxypropylated | DS = 0.13 |

*degree of substitution

TABLE 5

Concentration of starch after incubation for 22 hours.

| | Starches | | | | | | | | | |
|---|---|---|---|---|---|---|---|---|---|---|
| Bacteria | 1 | 2 | 3 | 4 | 5 | 6 | 7 | 8 | 9 | 10 |
| Cl. butyricum | 3.364 | 1.829 | 2.354 | 3.714 | 1.418 | 2.175 | 2.980 | 3.121 | 2.648 | — |

TABLE 5-continued

Concentration of starch after incubation for 22 hours.

| Bacteria | Starches | | | | | | | | | |
|---|---|---|---|---|---|---|---|---|---|---|
| | 1 | 2 | 3 | 4 | 5 | 6 | 7 | 8 | 9 | 10 |
| Bif. pseudolongum | 5.532 | 4.029 | 5.091 | 3.658 | 6.843 | 5.308 | 5.130 | 4.157 | 4.899 | 4.463 |
| Bif. bifidum | 5.245 | 4.132 | 7.035 | 4.503 | 5.437 | 4.950 | 4.375 | 4.720 | 5.091 | 5.454 |
| Bact. fragilis | 4.081 | 5.372 | 7.995 | 4.669 | 7.547 | 6.971 | 6.140 | 5.001 | 7.547 | 5.660 |
| Bact. vulgatus | — | 8.570 | 7.419 | 6.843 | 8.954 | 9.210 | 10.489 | 6.108 | 6.332 | 6.908 |
| Bif. strain X8AT2 | 10.106 | 6.492 | 10.00 | 5.532 | 6.268 | 7.931 | 9.850 | 6.843 | 5.820 | 5.916 |
| Lact. acidophilus | 8.75 | 10.501 | 10.50 | 10.50 | 92.84 | 10.50 | 10.07 | 10.50 | 10.50 | 95.54 |
| Lact. helviticus | 52.76 | 10.50 | 10.50 | 10.50 | 10.50 | 10.50 | 10.50 | 99.68 | 10.50 | 10.50 |

Starch concentrations after 22 hours incubation (mg/ml)
1: A.939 (D19) Hydroxypropylated; 2: A.938 (C79) Acetylated; 3: A.961 (D8) Octenyl succinated; 4: A.955 (D2) Carboxylated; 5: A.960 (D7) Succinated; 6: HA 008 (D2118) Unmodified; 7: A993 D42 Succinated; 8: A956 (D1) Carboxymethylated; 9: A995 (D57) Acetylated; 10: A965 (D9) Hydroxyproplated;

EXAMPLE 3

The effect of Co-culture with Amylolytic Bif. X8AT2 on the Growth of Lactobacillus sp in the Amylose Starch Medium The growth of *Lact. acidophilus* in the Hi-maize™ containing medium with or without the present of Bif. X8AT2 was compared. The growth medium contained 1% Hi-maize™ starch or glucose as the growth carbon and energy source. The medium was autoclaved at 121° C. for 15 minutes and strictly anaerobic conditions were used during the medium preparation. Overnight cultures (0.1 ml) of *Lact. acidophilus* and Bif. X8AT2 were inoculated into the serum tubes containing either glucose or Hi-maize™ starch based media. For the control *Lact. acidophilus* only was inoculated into the serum tubes. The tubes were then incubated at 37° C. for 24 hours. Samples were taken at 0, 2, 4, 6, 8, 10, 12 and 24 hours to enumerate the population of *Lact. acidophilus* by using standard series dilution method. The population of *Lact. acidophilus* was expressed as CFU/ml on MRS agar plates.

Since *Lact. acidophilus* can not degrade Hi-maize™ starch, the growth of *Lact. acidophilus* in the defined medium containing Hi-maize™ starch as the sole carbon source was very slow and resulted in low biomass. The improvement of the growth of *Lact. acidopliilus* in Hi-maize™ medium was observed when the strain was co cultured with the Hi-maize™ starch-utiliser, Bif. strain X8AT2 (FIG. 1). As can be seen in FIG. 1, a synergistic effect is demonstrated when the Bifidobacterial strain is inoculated with the Lactobacillus.

EXAMPLE 4

Mice were fed either normal mouse diet or a prepared diet containing either waxy starch, Hi-maize™ or modified Hi-maize™ (carbo.xvmethylated) and were orally dosed with 200 microlitres of Bifidobacterium sp strain X8AT2 or *Bifidobacterium bifidum* cultures. The composition of the mouse prepared diet is included in Table 6. Faecal samples were collected after continuous feeding from day 3 to day 8 of the diet plus the bifidobacteria. The major bacterial roups were enumerated using selective media and the total bacteria output for the groups were calculated. As can be seen in Table 7, Bacteroides numbers were enhanced significantly in mice when they were fed a modified resistant starch plus bifidobacteria compared to controls, which include mice fed resistant starch plus bifidobacteria. While it is established that Bacteroides of intestinal origin can ferment both starch (amylopectin) and resistant starch (amylose) reviewed by Salyers and Leedle (Salyers & Leedle, 1983), it is surprising to discover that a carboxymethylated amylose can significantly increase growth of the Bacteroides.

TABLE 6

Diets for mice probiotic feeding experiments.

| Test Groups | A | B | C | D | E |
|---|---|---|---|---|---|
| Starch | Waxy 400 | HA 400 | Carboxy-methyl 400 | HA 400 | None |
| Casein | 200 | 200 | 200 | 200 | |
| Canola oil | 25 | 25 | 25 | 25 | |
| Sunflower oil | 25 | 25 | 25 | 25 | |
| Sucrose | 150 | 150 | 150 | 150 | |
| Wheat bran | 100 | 100 | 100 | 100 | |
| Gelatin | 20 | 20 | 20 | 20 | |
| Mineral mix | 67 | 67 | 67 | 67 | |
| Vitamin mix | 13 | 13 | 13 | 13 | |
| Methionine | 2 | 2 | 2 | 2 | |
| Bacterial strain | X8AT2 | X8AT2 | X8AT2 | None | X8AT2 |

Waxy = waxy maize; HA = High amylose starch; Carboxy-methyl = Carboxymethylated high amylose starch. All weights are in grams. Bacterial cultures (100 microliters per day) were orally ingested by the mice with starch containing meals.

TABLE 7

Bacteroides population in mice feeding study (total bacteria output per day per mice).

| | Starches | | | | |
|---|---|---|---|---|---|
| | Group A | Group B | Group C | Group D | Group E |
| Bacteroides | 9.163 ± 0.42 | 8.961 ± 0.40 | 9.952 ± 0.357 | 8.961 ± 0.576 | 8.463 ± 0.569 |
| Mean Diff. (compare to group A) | | A-B: 0.202 | A-C: −0.789 | A-D: 0.202 | A-E: 0.699 |
| F-test | | none | $p < 0.05$ | none | $p < 0.05$ |
| Mean Diff. (compare to group E) | A-E: −0.699 | E-B: −0.498 | E-C: −1.489 | E-D: −0.497 | |
| F-test | $p < 0.05$ | $p < 0.05$ | $p < 0.05$ | $p < 0.05$ | |

Group A: Waxy starch plus X8AT2 — Bifidobacteria human isolates;
Group B: Hi-maize ™ starch plus X8AT2;
Group C: Carboxymethylated resistant starch plus X8AT2;
Group D: Hi-maize ™ starch plus *Bif. bifidum;*
Group E: Normal mice diet plus X8AT2

EXAMPLE 5 a) Four groups of six mice (Balb/c, SPF) were continuously fed with semisynthetic diets for 4 weeks. Group A received 40% waxy starch in the diet, and groups C and E had 40% modified starches D2 and D57, respectively in their diets. Group D was the Hi-maize™ starch group and group B was assigned as the control to be fed with normal mice diet. Two faecal samples were collected at the end of experimental period (4 weeks) to enumerate the population of Bifidobacterium by using propionic acid agar. Bifidobacteria were further identified by cell morphology under light microscopy. The population of Bifidobacterium was expressed as total output per day per mice.

The results from three experiments indicated that the specific pathogen free (SPF) mice used in the experiment were free of detectable bifidobacteria (<10[]3) and continued to be so for the 2 months as control animals (Table 8). It is very surprising, however, to find that when the mice shifted from normal mice diet to the starch diets, the population of bifidobacteria increased significantly. The degree of increase depended on the type of starch incorporated into the diets. Hi-maize™ starch diet yielded the greatest numbers of native bifidobacteria in the mice faeces, followed by the waxy starch diet Modified Hi-maize™ starch D57 demonstrated better results in the stimulation of the growth of bifidobacteria than modified Hi-maize™ starch D2. The results from previous experiments indicated that D2 starch mainly sustained the good growth of Bacteroides. The statistical analysis of the data is also presented in Table 8.

After the first stage of experiment in which the mice were fed with the experimental diet for 4 weeks, 200 ul of Bif. X8AT2 was orally dosed into mice for 5 days. Numbers of Lactobacillus from all of groups were quantified in the mice faeces at both stages of experiments by using Rogosa agar. The cell morphology of Lactobacillus were also checked under phase-contract microscopy.

It can be seen that the highest fermentability of starch was detected with *Cl. butyrium*. *Bif. bifidum* and *Bif. psuedologum* are also capable of hydrolysilg all of the starches. while human isolate Bif. X8AT2 preferred starch nos. 2, 4, 5, 8, 9 and 10. *Bact. fragilis* has a stronger amylolytic capability to degrade starches than *Bact. vulgatus*. The poorest genus is Lactobacillus, since both strains tested could only partially utilise the modified Hi-maize™ starch 1.

All of the mice were heavily colonised with dense populations of Lactobacillus. The influence of diets on faecal population of Lactobacillus is shown in Table 9. In general, none of the starch diets supported the increased growth of native Lactobacillus, in comparison with normal mice diets. Particularly low numbers of Lactobacillus were detected in the groups of mice fed with modified starches D2 and D57. The population of Lactobacillus, however, increased in the group of mice fed with Hi-maize™ diet when amylolytic bifidobacterial strain XBAT2 was associated with the mice.

TABLE 8

Native population of Bifidobacteria in mice fed with different starches diets (CFU log 10/g faeces)

| | Starches | | | | |
|---|---|---|---|---|---|
| | Group A | Group B | Group C | Group D | Group E |
| Bifido-bacterium | 7.48 ± 0.481 | 0 ± 0 | 1.475 ± 2.174 | 8.235 ± 0.46 | 6.432 ± 0.566 |
| Positive mice in the test group | 6/6 | 0/6 | 2/6 | 6/6 | 6/6 |
| Mean Diff. (compare to group A) | | A-B: 7.47 | A-C: −6.005 | A-D: −0.755 | A-E: −1.048 |
| F-test | | $p < 0.05$ | $p < 0.05$ | none | none |
| Mean Diff. (compare to group B) | B-A: −7.48 | | B-C: −1.475 | B-D: −8.235 | B-E: −6.432 |
| F-test | $p < 0.05$ | | $p < 0.05$ | $p < 0.05$ | $p < 0.05$ |

Group A: Waxy starch
Group B: Normal mice diet
Group C: Carboxymethylated amylose starch
Group D: Hi-maize ™ starch
Group E: Acetylated maize starch

TABLE 9

Lactobacillus population in the mice fed with different starches diets (CFU log 10/g wet faeces)

| | Starches | | | | |
|---|---|---|---|---|---|
| | Group A | Group B | Group C | Group D | Group E |
| Lactobacillus | | | | | |
| Period 1: | | | | | |
| Fed with experimental diets for 4 weeks | 7.596 ± 0.477 | 8.113 ± 0.532 | 7.423 ± 0.295 | 7.858 ± 0.367 | 7.309 ± 0.326 |
| Mean Diff. (compare to group B) | B-A: 0.517 | | B-C: −0.690 | B-D: −0.255 | B-E: −0.804 |
| F-test | none | | $p < 0.05$ | none | $p < 0.05$ |
| Period 2: | | | | | |
| Experimental diets plus Bifido-bacterium X8AT2 | 7.823 ± 0.397 | 7.782 ± 0.477 | 7.501 ± 0.319 | 8.031 ± 0.529 | 7.451 ± 0.673 |
| Mean Diff. (compare to group D) | D-A: 0.208 | D-B: 0.249 | D-C: 0.531 | | D-E: −0.580 |
| F-test | none | none | $p < 0.05$ | | $p < 0.05$ |

EXAMPLE 6 a) Material from human colon was diluted Wilkins Chargren broth (1:1000).

The mixtures were incubated 37° C. for 24 h and sampled at 0, 3, 6, 9, 12 and 24 h post inoculation.

The type of resident starch or modifications thereof will induce an alteration or stimulation of resident microbes. After 9 h incubation, Starch nos. 8 and 9. induced an increase in the bifidobacterial population (FIG. 2) followed by the bifidobacterial populations of cultures supplemented with Starch no. 1, 2, 10 and 7. Cultures supplemented with Starch no. 6 were less benefited, resulting in a relatively poor development of the bifidobacterial population. Starch no. 3 had only a moderate beneficial effect on bifidobacterial growth.

Figure 2:
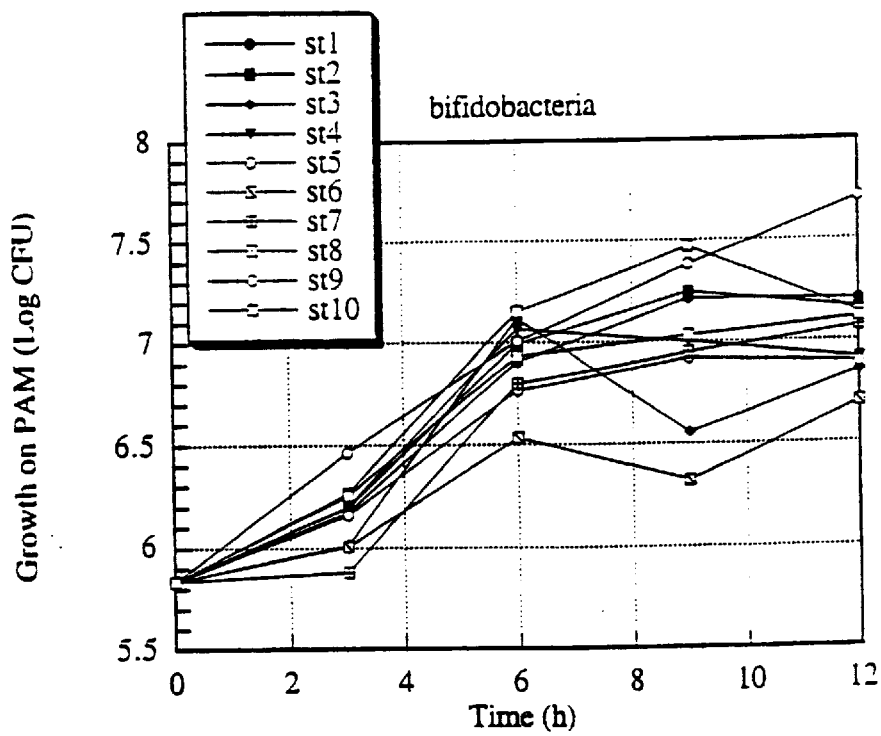
FIG. 2 shows enumeration of number of bifidobacteria in starch based medium inoculated with human faecal homogenates and incubated anaerobically at 37° C. for 12 hours. Individual starches according to the description in Table 4.
Figure 3:
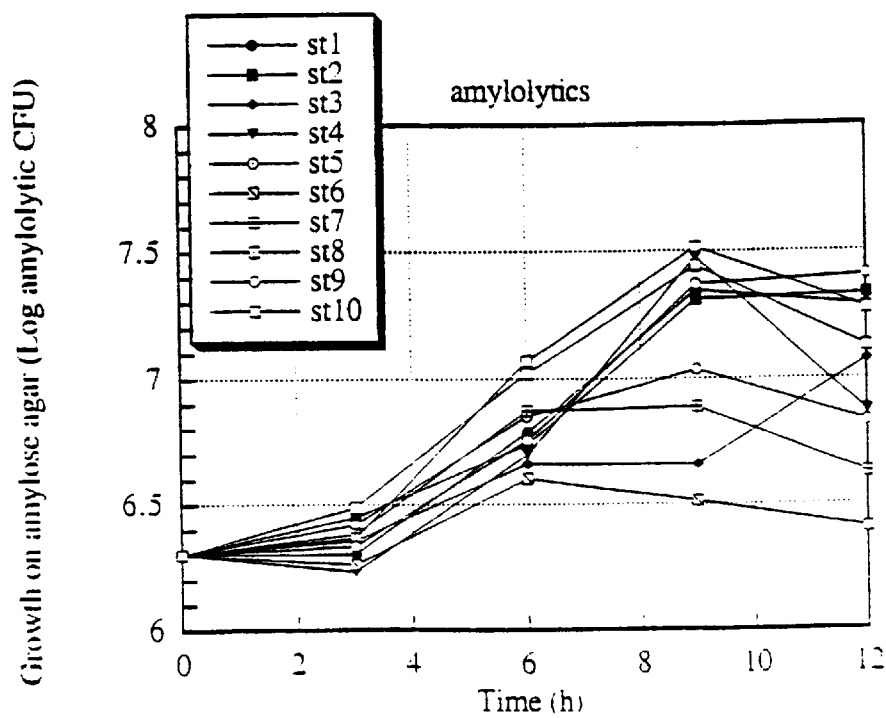
FIG. 3 shows enumeration of number of amylolytic bacteria in starch based media inoculated with human faecal homogenates and incubated anaerobically at 37° C. for 12 hours. Individual starches as in Table 4.
Figure 4:
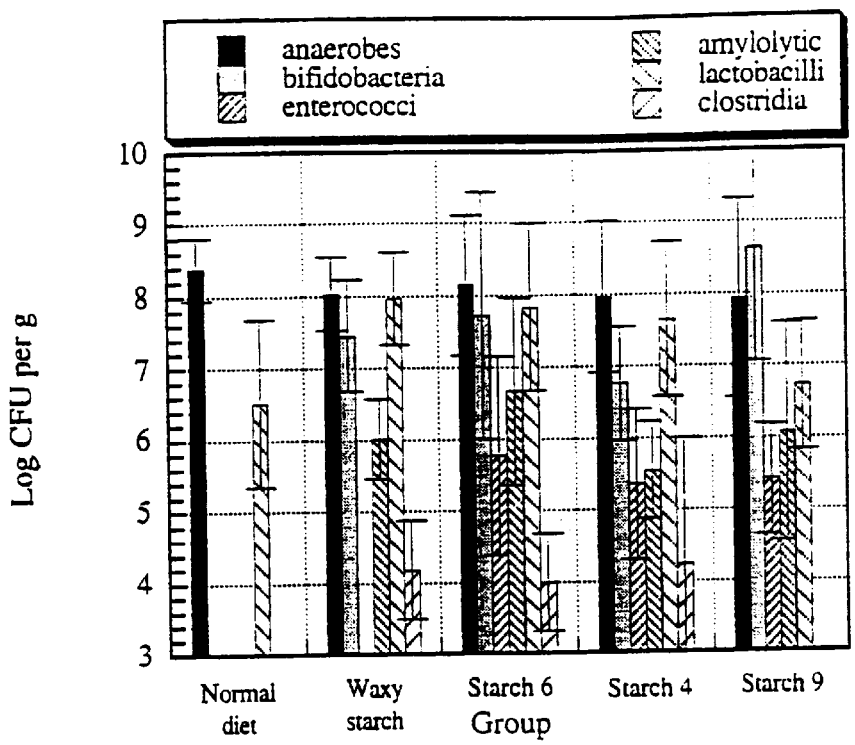
FIG. 4 shows enumeration of major bacterial groups in stomach contents from mice on various starch based diets (Table 4).
Figure 5:
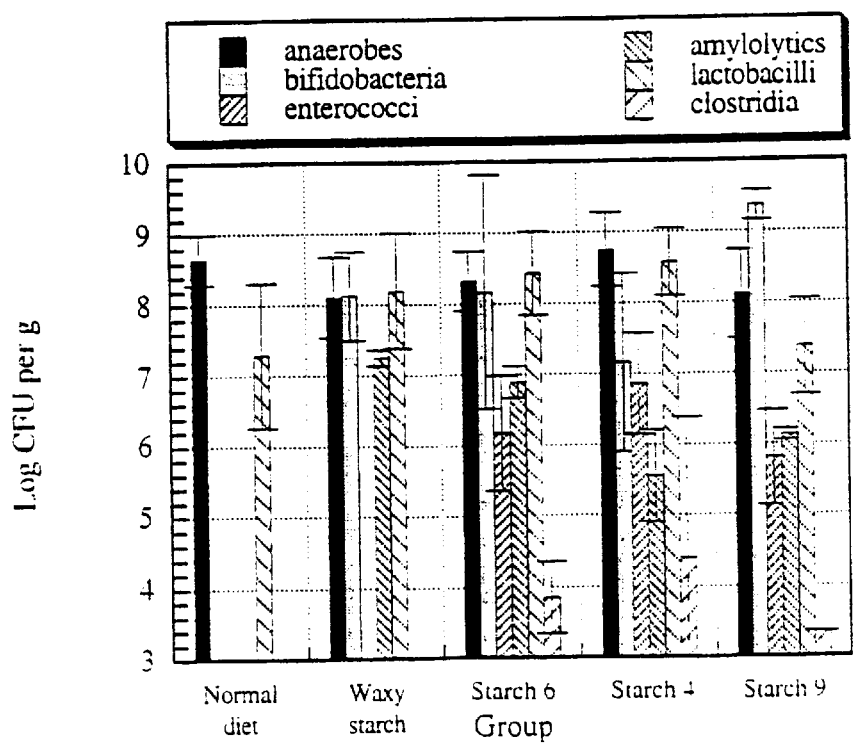
FIG. 5 shows enumeration of major bacterial groups in ileal contents from mice on various starch based diets (Table 4).
Figure 6:
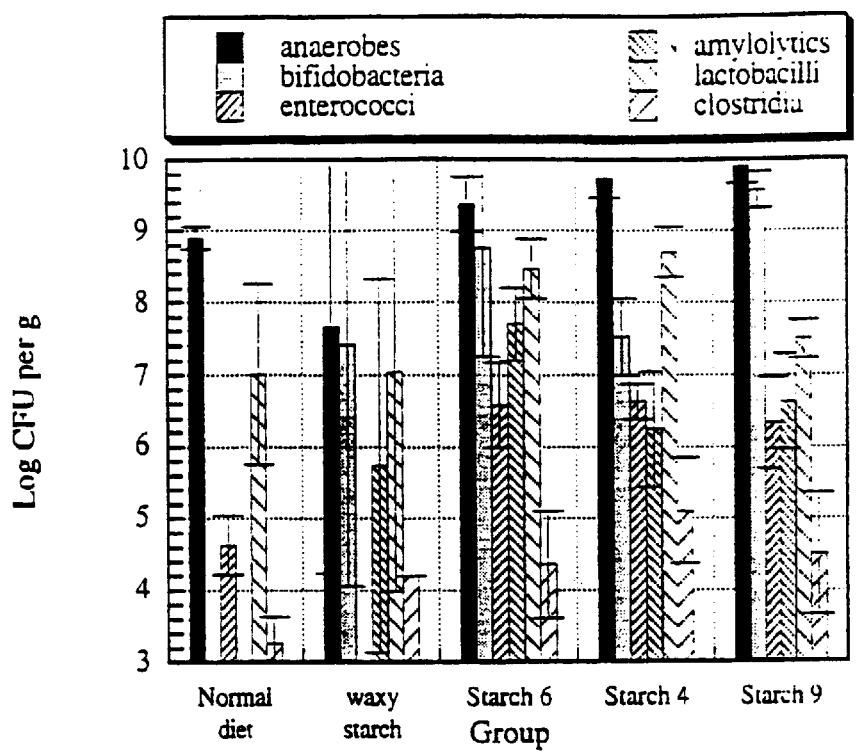
FIG. 6 shows enumeration of major bacterial groups caecal contents from mice on various starch based diets (Table 4)
Figure 7:
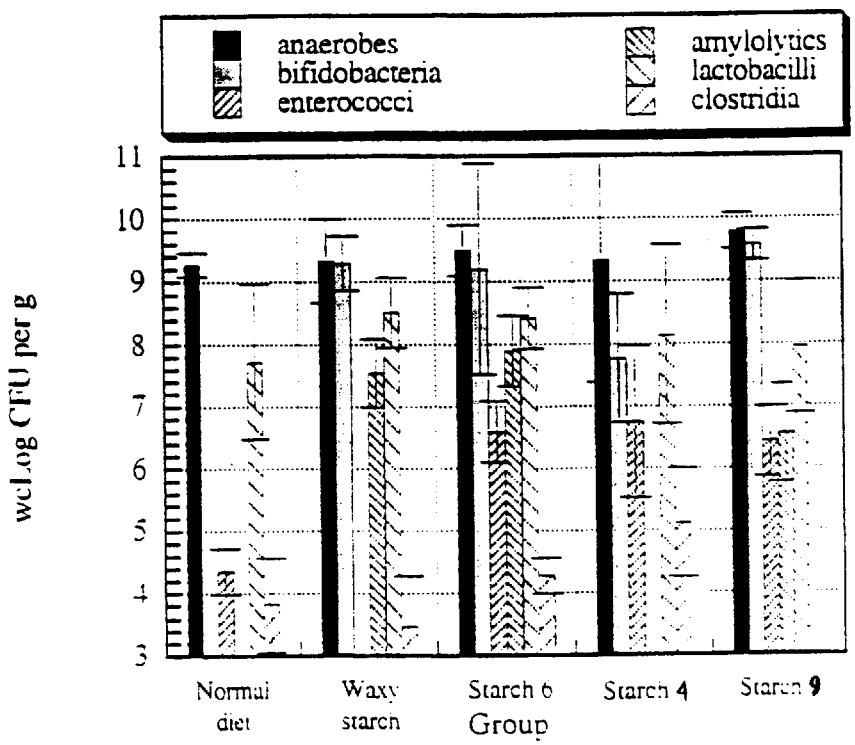
FIG. 7 shows enumeration of major bacterial group in colon contents from mice on various starch based diets (Table 4).

A large stimulation of the amylolytic microbial population (FIG. 3) was detected when either Starch nos. 8, 4, 10 or 9 were used as a source of carbon. In contrast, poor development of the bifidobacterial population was noted in cultures supplied with Starch nos. 6, 3, 7 and 5. A close correlation between growth response of amylolytic and bifidobacterial populations was noted (FIGS. 2 and 3).

EXAMPLE 7

Degradation of Starch nos. 1–10 by Human Faecal Microorganisms

The degradation of resistant starch and modifications thereof (Table 4) by human faecal microbes was studied. After 12 and 24 h incubation of faecal homogenates in media based on the starches in Table 4 the various degree of utilisation was determined (Table 10). There was a great variation in resistance to degradation. Starch nos. 1 and 8 were most efficiently degraded by the human faecal microbiota, which resulted in 0.31 and 1.8%, respectively starch remaining in the cultures 24 h post inoculation. Starch nos. 7 and 9 were less efficiently degraded, giving about 9% remaining starch in the final culture 24 h post inoculation. The most resistant starch was Starch no. 6. The difference in resistance to degradation was even more significant in cultures incubated for 12 h. At this point (12 h), six starches were assayed: Starch nos. 1, 4, 6, 7, 8 and 9. Starch no. 1 was of the starches the most easily degraded (2.74% remaining), followed by Starch no. 8 (5.3%). Starch no. 4 (23.4%). Starch no. 9 (44.50%), Starch no. 7 (79.7%) and Starch no. 6, the one most resistant to degradation. No degradation of starch no. 6 could be detected 12 h post inoculation (Table 10).

TABLE 10

Degradation of Starch nos. 1–10 by human faecal microorganisms.

| Type of Starch | Residual starch (%) | |
| --- | --- | --- |
| (Table 4) | 12 h post inoculation | 24 h post inoculation |
| 1 | 2.73 ± 0.46 | 0.31 ± 0.10 |
| 2 | N/A | 7.07 ± 1.24 |
| 3 | N/A | 8.57 ± 1.08 |
| 4 | 23.4 ± 4.72 | 5.59 ± 1.73 |
| 5 | N/A | 11.8 ± 2.86 |
| 6 | 119. ± 17.4 | 29.9 ± 8.57 |
| 7 | 79.2 ± 11.3 | 9.01 ± 2.85 |
| 8 | 5.26 ± 1.48 | 1.76 ± 0.34 |
| 9 | 44.5 ± 1.58 | 7.55 ± 0.95 |
| 10 | N/A | 9.38 ± 1.80 |

EXAMPLE 8

Hi-maize™ can be modified to various levels with chemical reagents, such as acetic anhydride. The degree of susceptibility to in vitro digestion by bacterial alpha-amylase and amyloglucosidase of Hi-maize™ and three acetylated starches from Hi-Maize™ was ascertained using the Megazyme Total Starch Assay Procedure (AA/AMG 6/95). Each starch was solubilised and the enzyme resistant "residue" recovered by centrifugation. The residue was then solubilised using DMSO and assayed as per the Megazyme resistant starch method. The results are shown in Table 11.

TABLE 11

Resistance of acetylated Hi-maize ™ starch to amylase digestion

| Starch type | Amylose content (%) dsb* | Acetyl value (%) dsb | Enzyme solubilised starch (%) dsb | Starch residue (%) dsb |
| --- | --- | --- | --- | --- |
| Hi-maize ™ | 85 | 0 | 93.8 | 6.2 |
| Starch A | — | 2.85 | 66.5 | 33.5 |
| Starch B | — | 4.39 | 58.5 | 41.5 |
| Starch C | — | 7.72 | 35.5 | 64.5 |

*dry solids basis

TABLE 12

Degradation of Starch nos. 1–10 by human faecal microorganisms [Percentage starch degraders of total faecal population growing on amylose plates (Sigma)] at various times post inoculation.

| | Amylolytic isolates in percentage of total CFU | | | |
| --- | --- | --- | --- | --- |
| | 3 h | 6 h | 9 h | 12 h |
| Starch 1 | 100 | 56 | 56 | 30 |
| Starch 2 | 90 | 36 | 69 | 65 |
| Starch 3 | 80 | 35 | 28 | 12 |
| Starch 4 | 87 | 35 | 61 | 29 |
| Starch 5 | 81 | 50 | 54 | 28 |
| Starch 6 | 88 | 58 | 16 | 7 |
| Starch 7 | 63 | 47 | 48 | 10 |
| Starch 8 | 72 | 66 | 67 | 56 |
| Starch 9 | 77 | 75 | 80 | 65 |
| Starch 10 | 72 | 73 | 58 | 21 |

EXAMPLE 9

This example demonstrates that various modifications of resistant starch as presented in Table 4 induce the development of microbes with varying amylolytic activity. (Starch no. 1 and 8 are soluble and could not be assessed in this study). This was assessed by relating the number of isolates that produced clearing zones on amylose agar to the total population (CFU) on amylose plates (in % of total), and the degree of amylolytic activity expressed by amylolytic isolates. This was assessed by measuring clearing zones developed around colonies with amylolytic activity. There was a great variation in capacity the human faecal microbiota to degrade the different starches. Starch nos. 2 and 3 were degraded by the highest percentage of the population (65%) followed by Starch no 8 which was degraded by 56% of the population (Table 12). Starches 3 and 6 were degraded by only 12% and 7% respectively.

Production of Short Chain Fatly Acids (SCFA)

Compared to the glucose control, the addition of starches (except Starch no. 11) resulted in a significant increase in the production of all investigated SCFA's.

The production of n-butyric acid was greatest in media containing Starch no. 8, followed by Starch no. 4, Starch no. 5, Starch no. 2, Starch no. 6 and media containing Starch no. 10 (Table 13).

The production of acetic acid was greatest in media containing Starch no. 8, followed by Starch no. 1, Starch no. 2, Starch no. 10, Starch no. 5 and media containing Starch no. 9.

The production of propionic acid was greatest in media containing Starch no. 8, followed by Starch no. 3, Starch no. 9, Starch no. 6, Starch no. 4 and media containing Starch no. 2.

The production of iso-butyric acid was greatest in media containing glucose, followed by Starch no. 7 and Starch no.

3. Iso-butyric acid could not be detected in cultures supplied with any other starches.

The production of iso-valeric acid was greatest in media containing Starch no. 6, followed by media containing Starch no. 4, Starch no. 9, Starch no. 8, Starch no. 5 and glucose.

Starch no. 8 promoted production of all major SCFA's (acetic, propionic and butyric acid), more that any of the other starch, that resulted in a butyric acid concentration that was about 1.5 times greater than for Starch no. 3 (Table 13).

TABLE 13

Production of Short Chain Fatty Acids from Starch nos. 1–11 and glucose, 24 h post inoculation with human faecal material.

| Type of carbon source | Short Chain Fatty Acid (mM) | | | | |
|---|---|---|---|---|---|
| | Acetic | Propionic | iso-Butyric | n-Butyric | iso-Valeric |
| Starch 1 | 40.7 ± 4.17 | 15.4 ± 1.21 | 0 | 11.5 ± 2.44 | 0.18 ± 0.37 |
| Starch 2 | 37.9 ± 0.44 | 15.8 ± 0.11 | 0 | 9.66 ± 0.37 | 0 |
| Starch 3 | 35.4 ± 0.95 | 18.5 ± 0.62 | 0.48 ± 0.95 | 8.28 ± 0.51 | 0.35 ± 0.40 |
| Starch 4 | 34.8 ± 0.71 | 16.2 ± 0.36 | 0 | 10.7 ± 0.34 | 0.53 ± 0.46 |
| Starch 5 | 37.0 ± 7.85 | 15.7 ± 4.65 | 0 | 10.4 ± 3.19 | 0.46 ± 0.40 |
| Starch 6 | 35.8 | 17.4 | 0 | 9.77 | 1.05 |
| Starch 7 | 34.1 ± 3.35 | 15.2 ± 0.36 | 0.79 ± 1.11 | 8.44 ± 0.07 | 0.30 ± 0.42 |
| Starch 8 | 54.4 ± 1.65 | 19.0 ± 0.33 | 0 | 12.7 ± 1.01 | 0.48 ± 0.68 |
| Starch 9 | 36.4 ± 0.90 | 17.7 ± 0.43 | 0 | 8.41 ± 0.17 | 0.97 ± 0.02 |
| Starch 10 | 37.6 ± 0.82 | 15.5 ± 0.82 | 0 | 9.51 ± 0.50 | 0 |
| Starch 11 | 22.5 ± 0.26 | 10.0 ± 0.77 | 0 | 4.74 ± 0.25 | 0 |
| Glucose | 31.0 ± 0.08 | 12.4 ± 1.09 | 3.05 ± 0.30 | 7.15 ± 0.92 | 0.41 ± 0.57 |

TABLE 14

Efficiency of starch degradation by the microbiota that colonises animals fed either Waxy starch, Starch nos. 4, 6 or 9.

| Animals fed | Degradation of dietary starch | | | Amylose |
|---|---|---|---|---|
| Starch: | Starch 4 | Starch 6 | Starch 9 | (Sigma) |
| 1 | + | + | +++ | + |
| 1 | + | − | + | − |
| 4 | +++ | ++ | ++ | + |
| 4 | ++++ | +++ | ++ | ++ |
| 6 | ++++ | ++++ | ++++ | ++ |
| 6 | ++++ | + | +++ | +++ |
| 9 | +++ | + | ++++ | +++ |

EXAMPLE 10

Specific pathogen free (SPF) mice were fed synthetic diets consistent with those presented in Table 6 but using waxy starch and starches 4, 6 and 9 (Table 4). Five animals per group were used and maintained in the diet for 2 weeks. Animals were sacrificed and the gastrointestinal tract was collected. Contents from the stomach, ileum, caecum and colon were collected, weighed and stored on ice for processing within an hour. The major bacterial groups were enumerated using routine selective media. The groups include the obligate anaerobes, lactobacilli, enterococci, coliforms. amylolytic bacteria, clostridia and bifidobacteria. Amylolytic activity was assessed for isolates from the mice on the various diets by ranking the zone of clearance around colonies on agar plates prepared using either amylose (Sigma) of starches 4, 6 or 9. Results are presented in FIGS. 4, 5, 6 and 7. It can be seen in these figures that the different starches will induce altered levels of specific groups of microbes at different sites in the tract. For example starch 6 and 4 stimulate lactobacillus from the stomach, ileum and caecum; starch 9 stimulates bifidobacterium in all sites samples; starch 4 stimulates endospore forming populations such as the clostridia in all sites sampled and suppresses the bifidobacterial numbers as all sites sampled; starch 9 suppressed endospore forming populations in all regions sampled.

EXAMPLE 11

Ex-germ free mice colonised with human faecal homogenates were fed a commercial animal diet. Material from gastrointestinal of germ free mice colonised with human microbes (gastric, ileal, caecal and colonic content) was diluted in Wilkins Charlgren broth (1/1000). The faecal microbial composition of the aninal that served as a source for inoculum is presented in Table 15. Diluted material was used as the inoculum for the starch media (Table 1) continuing the different resistant starches in Table 4. The mice gastrointestinal content mixes were sampled at 0 and 9 h post inoculation.

Figure 8:
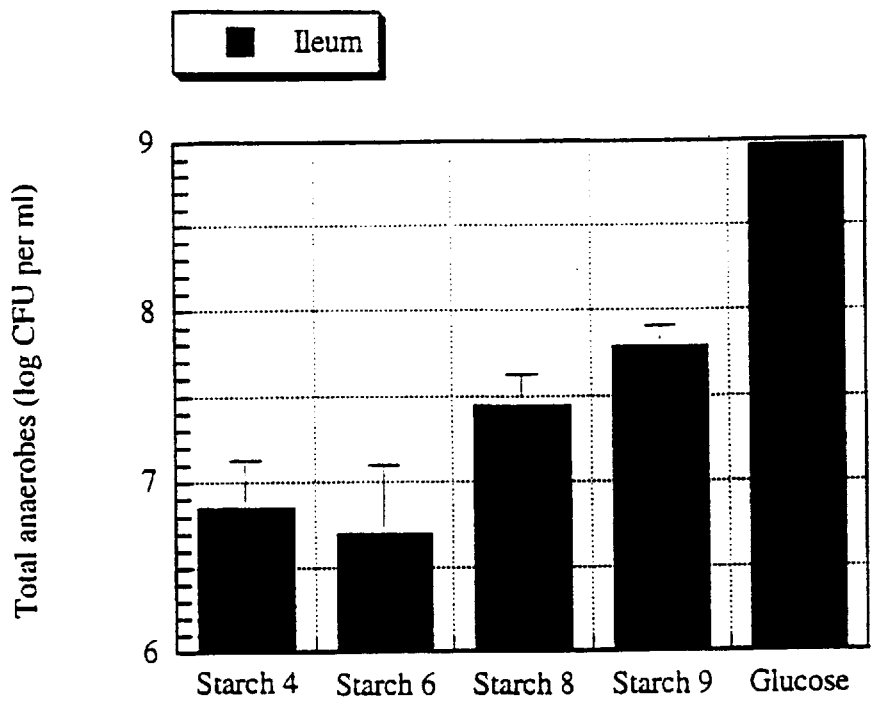
FIG. 8 shows the total anaerobic microbial population of ileal origin, 9 hours post inoculation in media containing starch nos 4, 6, 8, 9 and glucose.
Figure 9:
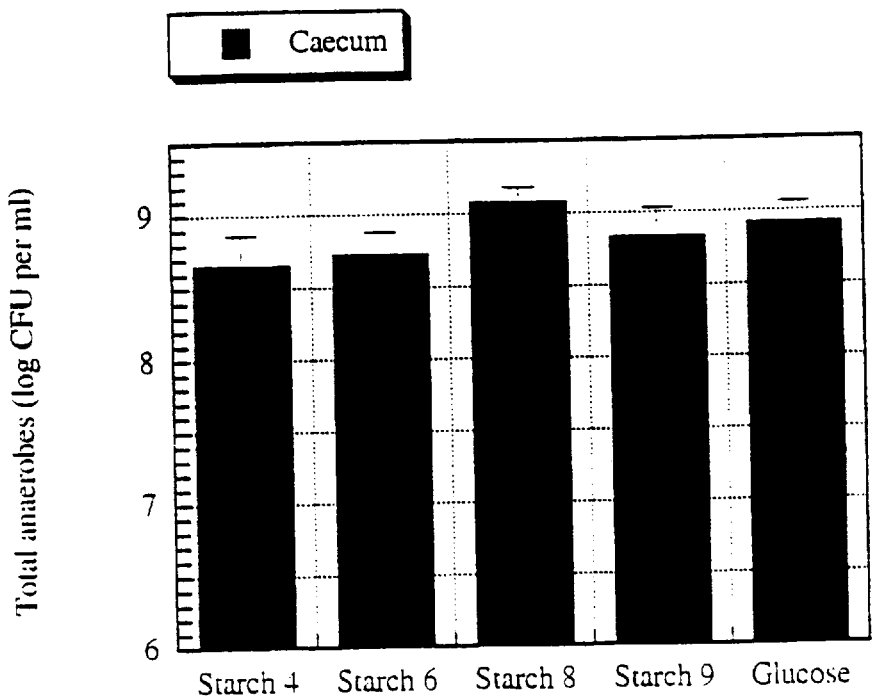
FIG. 9 shows the total anaerobic microbial population of caecal origin, 9 hours post inoculation in media containing starch nos 4, 6, 8, 9 and glucose.

The use of different modifications of resistant starches or unmodified starches could be used to control specific populations at different sites. This has been shown when gut contents from the stomach, ileum, caecum or colon of ex-germ-free mice colonised with human colon microflora were collected and inoculated into media containing the various starches as in Table 4. The mixtures were incubated anaerobically at 37° C. The concentrations of the major bacteria groups were enumerated and these included the total anaerobes, lactobacilli, bifidobacteria. It was shown that the modification influenced the levels of the different microbes. For example, starch 9 induced higher levels of obligate anaerobes in the ileum than were induced by starch 8 (FIG. 8) while starch 8 promoted higher levels of these obligate anaerobes in the caecum than were induced by starch 9 (FIG. 9).

TABLE 15

Microbial composition of faeces from mouse to be used

| Bacteria | CFU per g |
|---|---|
| Lactobacilli | <$10^3$ |
| Bifidobacteria | $1.7 \times 10^5$ |
| Enterococci | $3.7 \times 10^7$ |
| E. coli | <$10^3$ |
| Total anaerobes | $9.6 \times 10^9$ |
| Total amylolytic | <$10^3$ |
| endospores | $3.3 \times 10^3$ |

The resident bifidobacterial and amylolytic population may be replaced with new bfidobacterial and amylolytic populations. This will happen if the unrodfified Hi-maize™ (Starch no. 6) is supplied. Although bifidobacterial and amylolytic populations will be disadvantaged in the short term, animals fed Starch 6 (fro about 2.5 months) have a dense bifidobacterial and amylolytic population through out the gastrointestinal tract (FIGS. 4, 5, 6 and 7 and Table 14).

Uses

It has been shown that carboxymethylated resistant starch consumption resulted in greater numbers of faecal Bacteroides than unmodified resistant starch. It is well established that Bacteroides spp contribute to saccharide degradation in the large intestine, in particular polysaccharides degradation (Salyers, 1979). This would result in an increase in short chain fatty acids, which are used as metabolic fuel for the epithelial mucosa and for the host. In addition, there is a clear link between the levels of butyrate and the incidence of polyps and cancer (Young, 1996). Consequenitly. enhancing bacteroides numbers will lead to increased fermentation which will contribute to intestinal health and protect from the risks of colon cancer.

Other chemically modified starches may lead to enhancement of other beneficial bacteria in the large intestine. Consequently, one can use a modified resistant starch in the diet to achieve one or all of the following conditions:

i) as a general gut microflora stabiliser:

ii) in clinical conditions related to disturbances e.g. flora related irritable bowel syndrome and inflammatory bowel disease, Crohn's disease, diarrhoea;

iii) improved intestinal health e.g. of the epithelial mucosa;

iv) immunostimulating activities; and v) colon cancer

In addition, as discussed by Coates (Coates, 1988), resistant starch ingestion can cause a lowering of the pH which will lead to suppression of bacterial transformation of cholesterol and bile acids, thus affecting excretion of cholesterol and bile acids. Since the present inventors have found that modification of the resistant starch affected utilisation by specific microbes and the bacterial groups that were enhanced, modifications of the resistant starch could influence cholesterol and bile acid excretion levels.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of increasing the number or activity of a population of one or more microorganisms resident in the gastrointestinal tract of an animal, the method comprising administering orally to the animal a selected modified or unmodified resistant starch or mixtures thereof, the resistant starch being obtained from a starch having an amylose content of 50% w/w or more, or 27% w/w or more if a wheat or rice starch, in an amount effective such that the population of one or more microorganisms utilizes the resistant starch in a manner such that the number or activity of the population of one or more microorganisms increases in the gastrointestinal tract, wherein the method further comprises assaying for the levels of the microorganisms present in the gastrointestinal tract.

* * * * *